(12) United States Patent
Tjioe et al.

(10) Patent No.: US 6,274,731 B1
(45) Date of Patent: Aug. 14, 2001

(54) METHOD FOR PREPARING MELAMINE

(75) Inventors: Tjay T. Tjioe, Sittard; Hubertus J. M. Slangen, Stein, both of (NL)

(73) Assignee: DSM, N.V., Heerlen (NL)

( * ) Notice: Subject to any disclaimer, the term of this patent is extended or adjusted under 35 U.S.C. 154(b) by 0 days.

(21) Appl. No.: 09/453,021

(22) Filed: Dec. 2, 1999

Related U.S. Application Data

(63) Continuation of application No. PCT/NL98/00281, filed on May 15, 1998.
(60) Provisional application No. 60/048,478, filed on Jun. 3, 1997.

(30) Foreign Application Priority Data

Jun. 2, 1997 (NL) ................................................. 1006192

(51) Int. Cl.[7] .................... C07D 251/60; C07D 251/62
(52) U.S. Cl. ............................................................. 544/201
(58) Field of Search ............................................... 544/201

(56) References Cited

U.S. PATENT DOCUMENTS

| | | | |
|---|---|---|---|
| 4,109,090 | * 8/1978 | Van Hardeveld et al. | 544/201 |
| 4,465,832 | * 8/1984 | De Wit et al. | 544/201 |
| 4,565,867 | 1/1986 | Thomas et al. | 544/201 |
| 5,514,796 | 5/1996 | Best et al. | 544/201 |
| 5,514,797 | 5/1996 | Best et al. | 544/201 |
| 5,721,363 | * 2/1998 | Canzi et al. | 544/201 |

FOREIGN PATENT DOCUMENTS

| | | |
|---|---|---|
| 0 808836 A1 | 11/1997 | (EP) . |
| WO 96/20182 | 7/1996 | (WO) . |
| WO 96/20183 | 7/1996 | (WO) . |
| WO 96/23778 | 8/1996 | (WO) . |
| WO 97/20826 | 6/1997 | (WO) . |
| WO 97/47609 | 12/1997 | (WO) . |

* cited by examiner

*Primary Examiner*—Richard L. Raymond
*Assistant Examiner*—Venkataraman Balasubramanian
(74) *Attorney, Agent, or Firm*—Pillsbury Winthrop LLP

(57) ABSTRACT

Method for preparing melamine from urea via a high-pressure process in which solid melamine is obtained by transferring the melamine melt coming from the reactor to a vessel where the melamine melt is cooled with an evaporating cooling medium. The melamine melt comes from the melamine reactor at a temperature between the melting point of melamine and 450° C. and is sprayed into a cooling vessel, via spraying means, having an ammonia environment with an increased ammonia pressure and cooled by means of an evaporating cooling medium to form melamine powder. The melamine melt is thereby converted into melamine powder having a temperature of 270° C. or below after which the ammonia pressure is released and the melamine powder is cooled, at least for part of the cooling range, by the powder being set in motion mechanically and being cooled directly or indirectly and, if necessary, the melamine powder is cooled further.

17 Claims, No Drawings

METHOD FOR PREPARING MELAMINE

This is a continuation of PCT/NL98/00281, filed May 15, 1998. This application claims the benefit of U.S. Provisional Application No. 60/048,478, filed Jun. 3, 1997.

The invention relates to a method for preparing melamine from urea via a high-pressure process in which solid melamine is obtained by transferring the melamine melt coming from the reactor to a vessel where the melamine melt is cooled with an evaporating cooling medium.

Such a method is disclosed, inter alia, in EP-A-747366 which describes a high-pressure process for preparing melamine from urea. In particular, EP-A-747366 describes how urea is pyrolyzed in a reactor, operating at a pressure of from 10.34 to 24.13 MPa and a temperature of from 354 to 454° C., to produce a reactor product. This reactor product, containing liquid melamine, $CO_2$, and $NH_3$ and is transferred under pressure as a mixed stream to a separator.

In this separator, which is kept at virtually the same pressure and temperature as the reactor, the reactor product is separated into a gaseous stream and a liquid stream. The gaseous stream contains primarily $CO_2$ and $NH_3$ waste gases and melamine vapor. The liquid stream mainly comprises a melamine melt. The gaseous stream is transferred to a scrubber unit, while the liquid stream is transferred to a product-cooling unit.

In the scrubber unit, operated at temperature and pressure conditions nearly identical to the reactor conditions, the gaseous stream is scrubbed with molten urea. The heat transfer achieved in the scrubber unit both preheats the molten urea and cools the gaseous stream to a temperature from 177 to 232° C. The molten urea also scrubs the gaseous stream to remove the melamine vapor from the waste gases. The preheated molten urea, along with the melamine that was scrubbed from the $CO_2$ and $NH_3$ waste gases, is then fed into the reactor.

In the product-cooling unit, the melamine melt is cooled and solidified with a liquid cooling medium to produce a solid high purity melamine product without the need for additional purification. The preferred liquid cooling medium is one that forms a gas at the temperature of the melamine melt and at the pressure in the product-cooling unit. EP-A-747366 identifies liquid ammonia as the preferred liquid cooling medium with the pressure in the product-cooling unit being above 41.4 bar. Although according to EP-A-747366 the purity of the solid melamine product obtained using the disclosed process was greater than 99 wt %, this degree of purity has proven difficult to maintain continuously on a commercial scale. The inability to maintain a purity greater than 99 wt % is a drawback that renders the melamine produced less suitable for more demanding applications, particularly melamine-formaldehyde resins used in laminates and/or coatings.

The object of the present invention is to obtain an improved method for preparing melamine from urea, in which melamine is obtained directly from the reactor product as a dry powder having a high degree of purity. More particularly, the object of the present invention is to obtain an improved high-pressure process for preparing melamine from urea, in which melamine is obtained directly from the liquid melamine melt as a dry powder having a high degree of purity via cooling.

Applicant has found that high purity melamine can be continuously produced from the melamine melt coming from the melamine reactor, which has a temperature between the melting point of melamine and 450° C., by spraying the melamine melt via spraying means into a vessel and cooling the melamine melt by contact with an evaporating cooling medium in an ammonia atmosphere with an increased ammonia pressure whereby melamine powder is obtained with a temperature below 270° C., releasing the ammonia pressure and cooling the melamine powder, at least for part of the cooling range, by agitating the powder mechanically and cooling either directly, indirectly or some combination.

An increased ammonia pressure means an ammonia pressure greater than 1 MPa, preferably greater than 1.5 MPa, more preferably greater than 4.5 MPa and even more preferably greater than 6 MPa. The ammonia pressure is below 40 MPa, preferably below 25 MPa and more preferably below 11 MPa.

Melamine powder has poor flow and fluidization characteristics and a low temperature equalization coefficient (poor thermal conductivity). Standard cooling methods such as a fluidized bed or a packed moving bed cannot, therefore, be readily implemented on a commercial scale. We have found, however, that the color of the melamine powder, in particular, is adversely affected if the melamine remains at a high temperature for too long. Effective control of the residence time at high temperature has, therefore, proved critical. It is therefore important to be able to cool the melamine powder effectively.

Surprisingly, it proved possible to cool melamine powder, despite its poor flow and thermal conductivity characteristics, by utilizing mechanical agitation coupled with direct and indirect cooling. The term indirect cooling describes those instances in which the mechanically agitated melamine powder contacts a cooled surface. The term direct cooling describes those instances in which the mechanically agitated melamine powder contacts a cooling medium such as ammonia or an airstream. A combination of both direct and indirect cooling mechanisms is obviously also possible.

The melamine powder formed by spraying the melamine melt into the solidification vessel is held under an increased ammonia pressure at a temperature above 200° C. for a contact time. The duration of this contact time is preferably between 1 minute and 5 hours, more preferably between 5 minutes and 2 hours. During this contact time, the temperature of the melamine product can remain virtually constant or it may be cooled to a temperature above 200° C., preferably above 240° C., or, most preferably, above 270° C. An increased ammonia pressure means an ammonia pressure greater than 1 MPa, preferably greater than 1.5 MPa, more preferably greater than 4.5 MPa and even more preferably greater than 6 MPa. The ammonia pressure is below 40 MPa, preferably below 25 MPa and more preferably below 11 MPa. The melamine product may be cooled in the solidification vessel or in a separate cooling vessel.

The advantage of the method according to the present invention is the continuous production, on a commercial scale, of dry melamine powder with a purity above 98.5 wt %, and generally above 99 wt %, that has very good color characteristics. The high purity melamine produced according to the present invention is suitable for virtually any melamine application, including melamine-formaldehyde resins used in laminates and/or coatings.

The preparation of melamine preferably uses urea as the raw material, the urea being fed into the reactor as a melt and reacted at elevated temperature and pressure. Urea reacts to form melamine, and the by-products $NH_3$ and $CO_2$, according to the following reaction equation:

$$6CO(NH_2)_2 \rightarrow C_3N_6H_6 + 6NH_3 + 3CO_2$$

The production of melamine from urea can be carried out at high pressure, preferably between 5 and 25 MPa, without the presence of a catalyst, at reaction temperatures between 325 and 450° C., and preferably between 350 and 425° C. The by-products $NH_3$ and $CO_2$ are usually recycled to an adjoining urea factory.

The above-mentioned objective of the invention is achieved by employing an apparatus suitable for the preparation of melamine from urea. An apparatus suitable for the present invention may comprise a scrubber unit, a reactor having either an integrated gas/liquid separator or a separate gas/liquid separator, possibly a post-reactor, a first cooling vessel, and possibly additional cooling vessels. When a separate gas/liquid separator is used, the pressure and temperature of the separator are virtually identical to the temperature and pressure in the reactor.

In an embodiment of the invention, melamine is prepared from urea in an apparatus comprising a scrubber unit, a melamine reactor having either an integrated gas/liquid separator or a separate gas/liquid separator, a first cooling vessel, and a second cooling vessel. In this embodiment, the urea melt is fed into a scrubber unit operating at a pressure of from 5 to 25 MPa, preferably from 8 to 20 MPa, and at a temperature above the melting point of urea. This scrubber unit may be provided with a cooling jacket or internal cooling bodies to provide additional temperature control.

As it passes through the scrubber unit, the urea melt contacts the reaction waste gases coming from the melamine reactor or the separate gas/liquid separator. The reaction gases mainly consist of $CO_2$ and $NH_3$ and may include melamine vapor. The urea melt scrubs the melamine vapor from the $CO_2$ and $NH_3$ waste gases and carries this melamine along back to the reactor. In the scrubbing process, the waste gases are cooled from the temperature of the reactor, i.e. from 350 to 425° C., to from 170 to 240° C., the urea being heated to from 170 to 240° C. The $CO_2$ and $NH_3$ waste gases are removed from the top of the scrubber unit and may, for example, be recycled to an adjoining urea factory, where they can be used as raw materials for the urea production.

The preheated urea melt is drawn off from the scrubber unit, together with the melamine scrubbed from the waste gases, and transferred to the high pressure reactor operating at pressures between 5 and 25 MPa, and preferably between 8 and 20 MPa. This transfer may be achieved using a high-pressure pump or, where the scrubber is positioned above the reactor, gravity, or a combination of gravity and pumps.

In the reactor, the urea melt is heated to a temperature between 325 and 450° C., preferably between about 350 and 425° C., under a pressure between 5 and 25 MPa, preferably between 8 and 20 MPa, to convert the urea into melamine, $CO_2$, and $NH_3$. In addition to the urea melt, a certain amount of ammonia can be metered into the reactor as, for example, a liquid or hot vapor. The additional ammonia, although optional, may serve, for example, to prevent the formation of condensation products of melamine such as melam, melem, and melon, or to promote mixing in the reactor. The amount of additional ammonia supplied to the reactor may be up to 10 moles ammonia per mole of urea, preferably up to 5 moles ammonia per mole of urea, and, most preferably, up to 2 moles of ammonia per mole of urea.

The $CO_2$ and $NH_3$ produced in the reaction, as well as any additional ammonia supplied, collect in the separation section, for example in the top of the reactor or in a separate gas/liquid separator positioned downstream of the reactor, and are separated from the liquid melamine. If a separate, downstream gas/liquid separator is used, it may be advantageous for additional ammonia to be metered into this separator. The amount of ammonia in this case is 0.01–10 moles of ammonia per mole of melamine, and preferably 0.1–5 moles of ammonia per mole of melamine. Adding additional ammonia to the separator promotes the rapid separation of carbon dioxide from the reactor product, thus preventing the formation of oxygen-containing by-products. As described above, the gas mixture removed from the gas/liquid separator may be passed to the scrubber unit in order to remove melamine vapor and preheat the urea melt.

The melamine melt, having a temperature between the melting point of melamine and 450° C., is drawn off from the reactor or from the downstream gas/liquid separator and sprayed into a cooling vessel to obtain the solid melamine product. Prior to spraying, however, the melamine melt may be cooled from the reactor temperature to a temperature closer to, but still above, the melting point of melamine.

The melamine melt will be drawn off from the reactor at a temperature preferably above 390° C., and more preferably above 400° C., and will be cooled at least 5° C., and preferably at least 15° C., before spraying into the cooling vessel. Most preferably the melamine melt will be cooled to a temperature that is 5–20° C. above the solidification point of melamine. The melamine melt may be cooled in the gas/liquid separator or in a separate apparatus downstream of the gas/liquid separator. Cooling can take place by injection of a cooling medium, for example ammonia gas having a temperature below the temperature of the melamine melt, or by passing the melamine melt through a heat exchanger.

Furthermore, ammonia can be introduced into the melamine melt in such a way that a gas/liquid mixture is sprayed in the spraying means. In this case, the ammonia is introduced at a pressure above that of the melamine melt and preferably at a pressure between 15 and 45 MPa.

The residence time of the melamine melt between the reactor and the spraying means is preferably at least 10 minutes, and most preferably at least 30 minutes, and usually less than 4 hours.

The melamine melt, possibly together with ammonia gas, is transferred to a spraying means where it is sprayed into a first cooling vessel to solidify the melamine melt and form a dry melamine powder. The spraying means is an apparatus by which the melamine melt stream is converted into droplets, by causing the melt to flow at high speed into the first cooling vessel. The spraying means may be a nozzle or valve. The outflow velocity of the melamine melt from the spraying means is, as a rule, greater than 20 m/s, and is preferably greater than 50 m/s.

The cooling vessel contains an ammonia environment and operates at an increased ammonia pressure. The melamine powder thus formed having a temperature between 100° C. and the solidification point of melamine, preferably between 150° C. and 300° C., most preferably below 270° C. The melamine droplets from the spraying means are cooled by an evaporating cooling medium, for example, liquid ammonia, to produce melamine powder. The melamine melt may contain some portion of liquid ammonia with the remaining portion of the liquid ammonia being sprayed into the first cooling vessel.

The melamine powder formed by spraying the melamine melt into the cooling vessel is held under an increased ammonia pressure, at a temperature above 200° C. for a contact time. The duration of this contact time is preferably between 1 minute and 5 hours, more preferably between 5 minutes and 2 hours. During this contact time, the temperature of the melamine product can remain virtually constant or it may be cooled to a temperature above 200° C. An increased ammonia pressure means an ammonia pressure greater than 1 MPa, preferably greater than 1.5 MPa, more preferably greater than 4.5 MPa and even more preferably greater than 6 MPa. The ammonia pressure is below 40 MPa, preferably below 25 MPa and more preferably below 11 MPa.

At the end of the contact time, the melamine powder is cooled to a temperature below 270° C., by mechanically agitating the melamine powder and cooling it directly or indirectly. After the melamine powder has been cooled to a temperature below 270° C., the ammonia pressure is released to 0.05–0.2 MPa and, if necessary, the product may be cooled further.

The present method may be utilized in both batchwise and continuous processes. In the case of batchwise processing, two or more cooling vessels may be used with the melamine melt being sprayed sequentially into the various cooling vessels. Once a first cooling vessel contains the desired quantity of melamine powder, the spraying means for the first cooling vessel can be closed and the spraying means for the second cooling vessel opened. While the subsequent cooling vessels are being filled, the melamine powder in the first vessel can be treated further. In a continuous process, the liquid melamine will generally be sprayed in a first cooling vessel with the accumulating melamine powder being transferred into a second cooling vessel where the cooling step takes place. A hybrid of the batchwise and continuous methods may also be employed.

The melamine powder must be cooled from a temperature between the melting point of melamine and about 200° C. to a temperature below 100° C. During the spraying step the melamine melt is preferably cooled to a temperature between 10 and 60° C. below the solidification point. After the ammonia pressure has been released, the melamine powder is preferably cooled by at least 35° C., and more preferably 60° C., by being mechanically agitated and cooled directly or indirectly.

Cooling is effected with the aid of an apparatus provided with means for both mechanically agitating the melamine powder mechanically and for cooling the melamine powder directly or indirectly. Examples of means for mechanically agitating the melamine powder include a screw and rotating drum, a rotating bowl, rotating discs, rotating segmented discs, rotating pipes and the like.

The melamine powder can be cooled indirectly by contact with the cooled surface(s) of the fixed and/or moving parts of the cooling apparatus. The fixed and/or moving surface(s) of the apparatus may, in turn, be cooled with a cooling fluid such as water or oil. The effective heat transfer coefficient of a suitable cooling apparatus for indirectly cooling melamine powder is preferably between 10 and 300 W/m$^2$K, based on the cooling area of the apparatus. Preference is also given to the use of a cooling apparatus which comprises means having a cooling area of 50–5000 m$^2$.

The powder can be cooled directly by a gaseous or evaporating cooling medium being injected into the cooling vessel, preferably ammonia gas or ammonia liquid.

A combination of direct and indirect cooling techniques is preferred for cooling the melamine powder.

Once the melamine powder has been cooled to a temperature below 200° C., the ammonia pressure may be released. Preferably, ammonia gas is completely removed (to an amount below 1000 ppm, preferably below 300 ppm, and, most preferably, below 100 ppm) by blowing air through the melamine powder. The ammonia pressure may be released before, or in conjunction with, cooling the melamine powder from a temperature below 200° C. to ambient temperature.

The invention will be explained in more detail with reference to the following example.

EXAMPLE

Melamine melt having a temperature of 402° C. is introduced, via a spraying device, into a high-pressure vessel and cooled with liquid ammonia which is likewise sprayed in the vessel. The temperature in the vessel is 210° C. The ammonia pressure in the vessel varies between 6.8 and 9.2 MPa. The vessel is designed as a rotating drum provided with a wall which can be cooled, and provided with a gas inlet. After 2 minutes the ammonia pressure is released and the melamine powder is cooled to approximately 50° C. The cooling step to 50° C. took 7 minutes. The end product contains 0.4 wt % of melam and less than 0.2 wt % of melem.

COMPARATIVE EXAMPLE

Melamine melt of 400° C., held in a tube under an ammonia pressure of 13.6 MPa, is rapidly cooled to ambient temperature by the closed tube being brought into contact with a mixture of ice and water. The end product contains 1.4 wt % of melam and 0.4 wt % of melem.

What is claimed is:

1. A method for preparing melamine from urea via a high-pressure process by which solid melamine is obtained comprising steps:
    (a) forming a melamine melt, the melamine melt having a temperature between 450° C. and the melting point of melamine;
    (b) spraying the melamine melt into a vessel, the vessel having an ammonia environment at an elevated ammonia pressure, to form droplets of melamine melt;
    (c) cooling and solidifying the droplets of melamine melt with an evaporating cooling medium, the evaporating cooling medium being introduced into the vessel separately from the melamine melt to form melamine powder having an intermediate temperature of 270° C. or less;
    (d) releasing the ammonia pressure and cooling, either directly or indirectly, the melamine powder to a final temperature, the difference between the intermediate temperature and the final temperature defining a cooling range; and
    (e) mechanically agitating the melamine powder during at least a portion of the cooling range.

2. A method according to claim 1, wherein the melamine powder remains under increased ammonia pressure for a contact time of between one minute and five hours, the melamine powder remaining at virtually the same temperature, or optionally being cooled, during the contact time.

3. A method according to claim 1, wherein the melamine melt is sprayed via spraying means within a vessel into an ammonia environment having a pressure greater than 1 MPa.

4. A method according to claim 1, wherein the ammonia pressure is maintained until the melamine powder reaches an intermediate temperature below 240° C.

5. A method according to claim 4, wherein the ammonia pressure is maintained until the melamine powder reaches an intermediate temperature below 200° C.

6. A method according to claim 1, wherein the melamine powder remains under increased ammonia pressure for a contact time of between five minutes and two hours.

7. A method according to claim 1, wherein the melamine powder remains in contact with ammonia at a pressure of greater than 1 MPa.

8. A method according to any one of claims 1–7, wherein the melamine powder is cooled by means of an apparatus provided with means for agitating powder mechanically and provided with means for cooling the melamine powder directly or indirectly.

9. A method according to claim 8, wherein the means for mechanically agitating the melamine powder comprises a rotating screw, drum, bowl, discs, disc segments or pipes.

10. A method according to claim 8 or 9, wherein the apparatus has an effective heat transfer coefficient of 10–300 $W/m^2K$, based on the cooling area.

11. A method according to claim 8 or 9, wherein the apparatus has a cooling area of 50–5000 $m^2$.

12. A method according to claim 8 or 9, wherein the cooling is carried out at a pressure of 0.05–0.2 MPa.

13. A method according to claim 2, wherein the melamine melt is sprayed by a spraying means within a vessel into an ammonia environment at a pressure greater than 1 MPa.

14. A method according to claim 2 or 3, wherein the ammonia pressure is released if the melamine powder has a temperature below 240° C.

15. A method according to claim 2, 3, 4 or 5, wherein the powder remains in contact with ammonia over a period of five minutes to two hours.

16. A method according to claim 10, wherein the apparatus has a cooling area 50–5000 $m^2$.

17. A method for preparing melamine comprising the steps of:

reacting urea in a high-pressure melamine reactor to form a melamine melt, the melamine melt having a temperature between the melting point of melamine and 450° C.;

transferring the melamine melt from the melamine reactor to a first spraying means;

feeding the melamine melt through the first spraying means into a cooling vessel at a feed rate sufficient to form droplets of melamine melt, the cooling vessel containing an ammonia environment at an elevated pressure and a temperature of less than 270° C.;

feeding an evaporating cooling medium through a second spraying means into the cooling vessel, the second spraying means being positioned and configured in such a way as to cause the evaporating cooling medium to intermix with and contact the droplets of melamine melt;

solidifying the droplets of melamine melt to form melamine powder, the melamine powder having an initial temperature at least 10° C. less than the solidification temperature at the prevailing pressure;

cooling the melamine powder, utilizing direct or indirect cooling, to an intermediate temperature not greater than 270° C., the initial temperature and the intermediate temperature defining a first cooling range;

maintaining the ammonia pressure within the cooling vessel until the melamine powder has reached the intermediate temperature, the time during which the ammonia pressure is maintained defining a contact period;

reducing the ammonia pressure within the cooling vessel after the melamine powder reaches a temperature equal to or below the intermediate temperature;

further cooling the melamine powder from the intermediate temperature to a final temperature of less than 50° C., the intermediate temperature and the final temperature defining a second cooling range;

mechanically agitating the melamine powder over at least a portion of the second cooling range; and removing the melamine powder from the cooling vessel.

* * * * *